United States Patent [19]

Miller et al.

[11] Patent Number: 5,306,285
[45] Date of Patent: Apr. 26, 1994

[54] SURGICAL SAW BLADE

[75] Inventors: Alex M. Miller, Savannah, Ga.; Robert L. Stranahan, Ventura, Calif.

[73] Assignee: Komet Medical, Savannah, Ga.

[21] Appl. No.: 55,015

[22] Filed: Apr. 30, 1993

[51] Int. Cl.⁵ .............................................. A61B 17/14
[52] U.S. Cl. .................................... 606/177; 606/178; 30/355; 30/357
[58] Field of Search ................. 606/82, 176, 177, 178, 606/179; 30/353, 355, 357, 318, 166.3

[56] References Cited

U.S. PATENT DOCUMENTS

| | | | |
|---|---|---|---|
| 2,112,271 | 3/1938 | Dalkowitz | 30/357 |
| 2,757,697 | 8/1956 | Simmons et al. | 30/357 |
| 3,905,374 | 9/1975 | Winter | 606/178 |
| 4,768,504 | 9/1988 | Ender | 606/177 |

Primary Examiner—Tamara L. Graysay
Attorney, Agent, or Firm—Lowe, Price, LeBlanc & Becker

[57] ABSTRACT

A surgical saw blade comprises a cutting edge, blade body and hub for connecting the blade body to a handpiece. The cutting edge comprises two rows of cutting teeth. Each tooth has a face and an opposing hollow trough at the base thereof, the distal end of the trough terminating at beveled sides. The beveled sides and face opposing the hollow trough terminate at a cutting point. The hollow trough and cutting point combine to provide a straight, fast and accurate cut with no cutting debris build up. The dispersion of cutting debris dramatically reduces the danger of thermal necrosis, produces a cooler cut and extends the saw blade life.

12 Claims, 2 Drawing Sheets

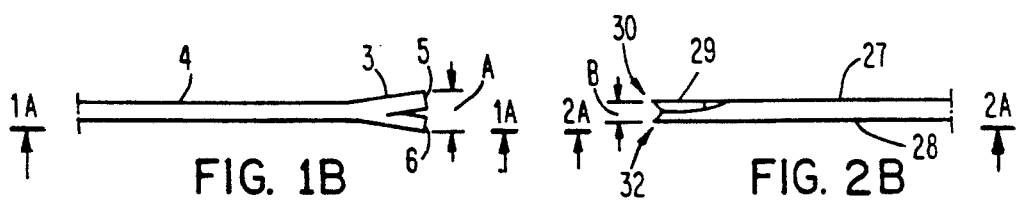
FIG. 1B PRIOR ART
FIG. 2B
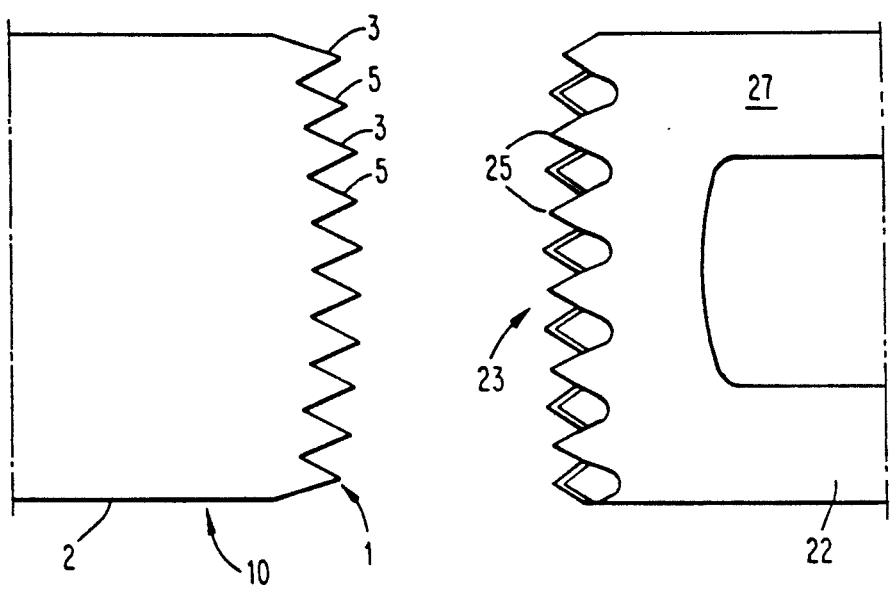
FIG. 1A PRIOR ART
FIG. 2A
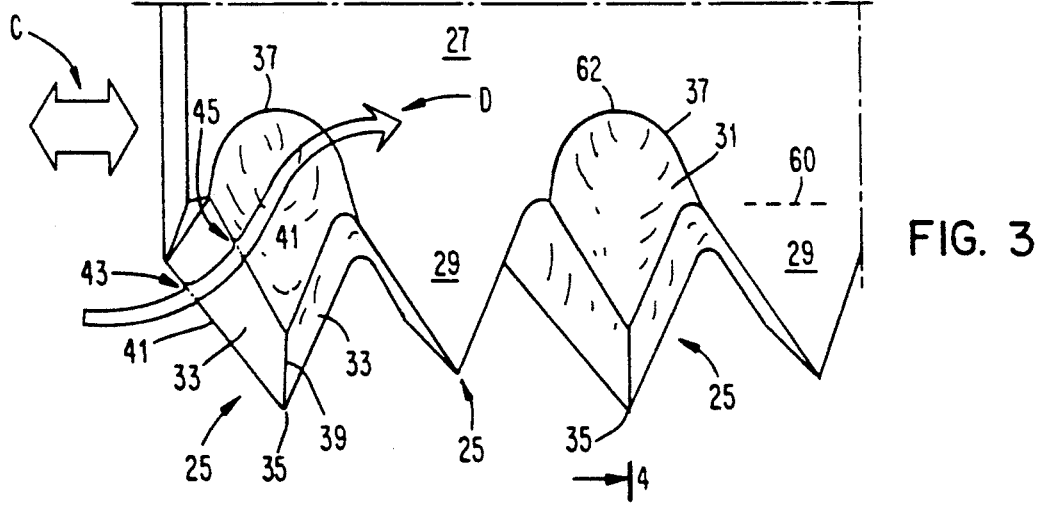
FIG. 3
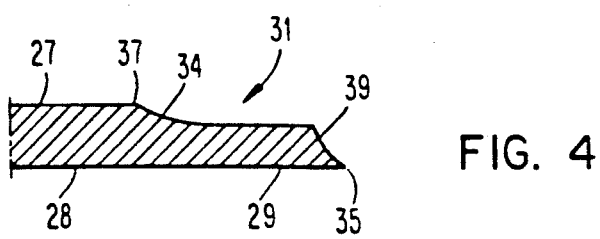
FIG. 4

SURGICAL SAW BLADE

FIELD OF THE INVENTION

The present invention is directed to an improved surgical saw blade and, in particular, to a blade having a double row of cutting teeth, each tooth having a bevel and a hollow trough to improve blade cutting performance.

BACKGROUND ART

In the prior art, it is known to use surgical saw blades in conjunction with a blade oscillating tool to remove tissue, cartilage and/or bone.

In knee surgery, saw blades are used in conjunction with slotted jigs which may be fixed to a femur and act as a blade guide. Typically, prior art saw blades include a plurality of teeth which are cant or set in an angled configuration. This type of surgical blade is shown in FIGS. 1A and 1B and is generally designated by the reference numeral 10. The surgical blade 10 is seen to include a cutting edge 1 and a blade body 2. The cutting edge comprises a series of alternating teeth 3 and 5, respectively. As can be seen from the side view, the teeth 3 are angled with respect to the blade surface 4 with the teeth 5 having a reversed cant or set as compared to the teeth 3.

These types of saw blades are disadvantageous in that the cutting edge 1 of the blade is 30 to 40% thicker than the blade body itself. This thicker cutting edge requires a wider slot in a surgical jig to permit insertion of the blade therethrough for contact with the tissue or bone to be cut. As a result of the wider slot, play exists between the slot faces and the blade body which can result in unwanted variances in cutting of tissue and/or bone.

The thicker cutting edge also contributes to increased bone loss which interferes with delicate cutting operations. These types of prior art blades also have a tendency to build up heat which causes thermal necrosis. The heat build up also contributes to wear and tear on the handpiece oscillating the blade as well as premature dulling of the blade edges.

In response to these deficiencies in prior art blade designs, a need has developed to provide a surgical saw blade which minimizes thermal necrosis, provides a cleaner and faster cut and further provides a more durable cutting edge giving longer useful blade life.

In response to this need, the present invention provides an improved surgical saw cutting blade overcoming the above-mentioned deficiencies.

SUMMARY OF THE INVENTION

It is a first object of the present invention to provide an improved surgical saw blade, in particular, for use in knee surgery or the like.

Another object of the present invention is to provide an improved surgical saw blade having a cutting tooth design which provides a faster and more efficient cut which minimizes the danger of thermal necrosis.

It is a further object of the present invention to provide a surgical saw blade having a novel tooth design which channels cutting debris away from the cutting teeth to enhance the blade cutting ability.

Another object of the present invention is to provide a surgical saw blade having a minimal off set at the cutting edge thereof to enhance use in surgical jigs for procedures such as knee surgery.

Other objects and advantages of the present invention will be apparent as the description thereof proceeds.

In satisfaction of the foregoing objects and advantages, there is provided a surgical saw blade comprising a blade body having opposing side surfaces and a cutting edge on the distal end of the blade. The saw blade also includes a hub for connecting the blade body to a handpiece or tool adapted to oscillate the blade for surgical use.

The cutting edge comprises a plurality of teeth, each tooth further comprising a generally flat face extending from one of the opposing side surfaces and terminating at a cutting point. Each tooth also includes a hollow trough having a generally concave surface which is aligned with the other side surface of the blade so as to in opposing relationship with the flat face of the tooth. The teeth are arranged in a pair of rows such that a flat face of a given tooth is adjacent the hollow trough of an adjacent tooth.

Each tooth may also include a pair of beveled sides disposed between a portion of the hollow trough and the flat face. The beveled sides join at a terminating edge which joins the cutting point at the distal end of the tooth.

In a preferred embodiment, the cutting edge of the inventive saw blade is between about 0.003 and 0.004 inches thicker than the blade body. This slight increase in thickness provides improved efficiency during cutting action. The cutting edge can have a width approximating the width of the blade body.

BRIEF DESCRIPTION OF DRAWINGS

Reference is now made to the drawings accompanying the invention wherein:

FIGS. 1A and 1B are a top and side view of a prior art surgical blade;

FIGS. 2A and 2B are a top and side view of a first embodiment of the inventive surgical saw blade;

FIG. 3 is a perspective view of a portion of the surgical saw blade depicted in FIG. 2 enlarged to show greater detail;

FIG. 4 is a cross-sectional view along the line IV—IV in FIG. 3;

DESCRIPTION OF THE PREFERRED EMBODIMENTS

Figure 5A:
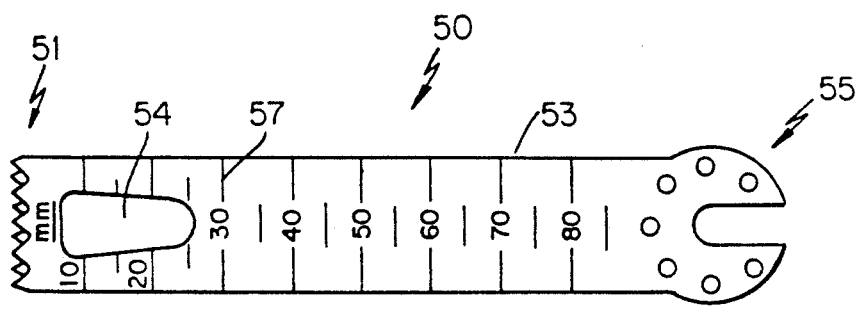
FIGS. 5A–5C are top views of alternative embodiments of the inventive surgical saw blade.

The present invention provides many advantages over prior art surgical saw blades as will be described hereinafter. Wither reference now to FIGS. 2A and 2B, a first embodiment of the inventive surgical saw blade is generally designated by the reference numeral 20 and includes a cutting edge 23 and a blade body 22. The cutting edge comprises a plurality of cutting teeth. Each of the cutting teeth is designated by the reference numeral 25.

The blade body 22 includes opposing surfaces 27 and 28. The cutting teeth 25 are arranged in a pair of rows. The first row, designated by the reference numeral 30, is generally aligned with the surface 27 with the second row 32 aligned with the opposing surface 28. As will be described hereinafter, these two rows enhance the accuracy and efficiency of the cut produced by the cutting edge 23.

With reference now to FIGS. 3 and 4, each of the cutting teeth 25 includes a generally flat face 29 extending from one of the opposing surfaces 27 or 28. The flat face 29 of each tooth is preferably off set from respective planes coinciding with the opposing surfaces 27 and 28. This off set, corresponding to the thickness "B" in FIG. 2B, results in a thickness increase of the cutting edge 23 of from about 0.003 to 0.004 inches greater than the thickness of the blade body 22. A more preferred off set or increase in thickness is 0.004 inches. It has been discovered that this minimal increase in thickness maximizes the efficiency of the cutting edge 23 during oscillation of the blade.

Each tooth 25 also includes a hollow trough 31. The hollow trough 31 has a generally concave surface 34 which generally opposes the flat face 29 of the tooth, see FIG. 4. The hollow trough 31 joins the planar surface 27 at semicircularly-shaped edge 37. A similar edge is formed for hollow troughs (not shown) joining the opposing surface 28 of the blade body 22.

Each tooth 25 also includes a pair of beveled surfaces 33 disposed between each hollow trough 31 and flat face 29. The beveled surfaces 33 terminate in an edge 39, the edge 39 further terminating at a distal end cutting point 35 of each tooth. As will be described hereinafter, the cutting point 35 functions to set the initial cut to hold and guide the cutting teeth during cutting action.

The surgical saw blade of the present invention provides many advantages over prior art surgical saw blades. First, and with reference to FIGS. 1A and 2A the inventive saw blade eliminates or reduces the increase in cutting edge thickness as compared to the blade body. In FIG. 1B the thickness of the prior art blade cutting edge is represented by the letter "A" with the thickness of the inventive saw blade depicted in FIG. 2B represented by the letter "B". A slot for guiding the prior art saw blade, such as a conventional femoral cutting guide must be sized to accommodate the 30% to 40% thicker cutting edges of prior art blades. With the inventive saw blade, and since each of the tooth faces 29 is generally aligned with one of the surfaces of the saw blade, the slot dimensions can closely parallel the blade body dimensions to reduce or eliminate play during a surgical procedure and provide a more accurate cut.

As can be seen from Prior Art FIG. 1A, the distal end of each cutting tooth forms an edge 6. In contrast, each tooth of the inventive saw blade terminates at a cutting point 35, see FIG. 3. By each tooth having a "diamond-cut" to a point, the initial cut of the blade is set by the point of each tooth. As the depth of the cutting increases, this set holds and guides the tooth flank. By holding and guiding the tooth flank, a straight and accurate cut is attained with minimal cavitation or dancing. By providing the cutting point in a set of two rows, further stabilization of the blade is achieved, with further enhancement of the accuracy of the cut.

The inventive blade, by the point-guided cutting action and reduced thickness at the cutting edge cuts appreciably faster than prior art blades with a minimal resistance. This maximum speed and accuracy permits cutting the narrowest of widths, and even further permits surface shaving of minute amounts of bone, for example, 0.5 millimeters or less.

In use, and still with reference to FIG. 3, the cutting teeth oscillate as shown by the arrow C. During oscillation of the cutting teeth, it has been discovered that the hollow trough 31 at the base of each tooth 25 improves cutting action by channeling cutting debris away from the cutting edges 41 of each tooth.

The arrow D, also representing tissue being cut, illustrates the cutting action and channeling away of cutting debris. As the tooth 25 moves opposite the direction indicated by arrow D, cutting occurs at reference numeral 43 and 45. The cut debris then flows into the trough 31, out and upwardly away from the cutting teeth 25. By eliminating debris build-up in the cutting tooth area, the blade cuts cooler which minimizes the danger of thermal necrosis at the surgical site. Reduced temperatures during cutting also reduce wear and tear on the handpiece oscillating the cutting blade. Removal of the debris also reduces abrasion against the cutting blade surfaces which results in increased durability of the sharpest cutting conditions and extended blade life.

In a preferred embodiment the teeth facets, i.e. face 29 form a 30° angle. The beveled surfaces 33 are also preferately 30+ as measured by a plane parallel to leveled surface 33 and perpendicular to surface 27. The face 29 can have a length of 0.08 inches as measured from its base 60 to the cutting point. The hollow trough can measure about 0.12 inches from its terminating edge 62 to the cutting point. Of course, other dimensions may be utilized for the various tooth components. The hollow trough is preferably ground to a radius of curvature of 0.12 inch for a blade thickness of 0.050 inches or 0.22 inches for a 0.035 inch blade thickness. Of, course, other radii may be used.

Figure 5B:
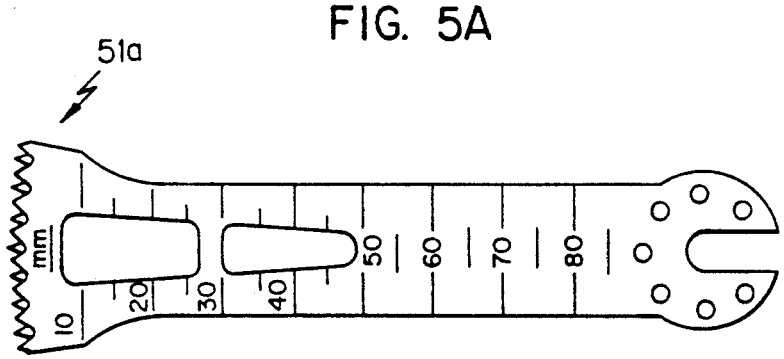
Figure 5C:
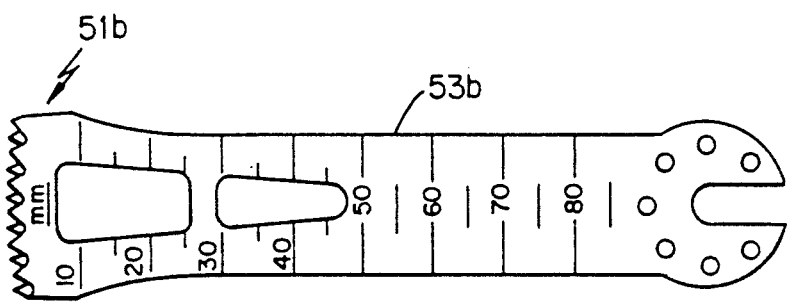

FIGS. 5A-5C depict alternative embodiments of the inventive saw blade. In FIG. 5A, designated by the reference numeral 50, the inventive saw blade includes cutting edge 51, blade body 53 and hub 55. The hub 55 is designed to connect to a handpiece which powers and oscillates the surgical blade during use. Hub 55 corresponds to a "Zimmer ®" hub. The blade 50 can also include indicia 57 thereon to indicate cutting depth. In this embodiment, the width of the cutting edge 51 approximates the width of the blade body 53. The opening 54 contributes to weight reduction of the blade. As shown in FIGS. 5B and 5C, more than one opening may be used.

FIGS. 5B and 5C depict embodiments similar to that depicted in FIG. 5A with different cutting edge configurations. In FIG. 5B, a cutting edge 51a is shown having a flared configuration. In FIG. 5C, the cutting edge 51b has a constant width which is greater than the width of the blade body 53b.

Figure 6A:
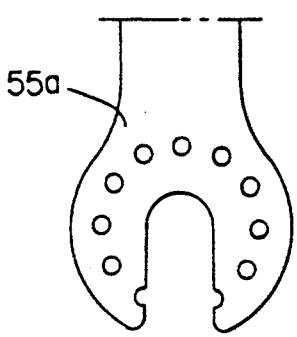
FIGS. 6A–6C show different types of hubs adapted for use with the inventive surgical saw blade.
Figure 6B:
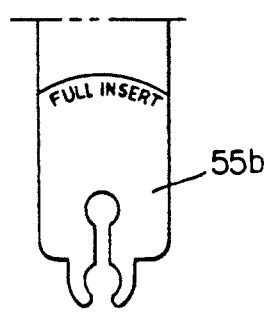
Figure 6C:
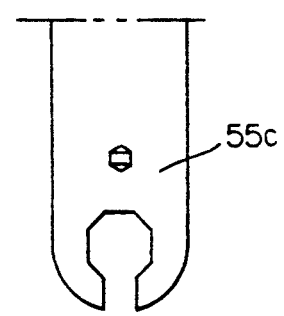

FIGS. 6A-6C show alternative hub configurations which are adapted for use with the inventive surgical saw blade. In FIG. 6A, a Stryker ® hub 55a is depicted with FIG. 6B showing a Stryker ® System 2000 hub 55b. FIG. 6C depicts a 3-M hub for use with the inventive surgical saw blade. Since these hubs are presently used in other surgical saw blades, a further description thereof is not deemed necessary. It should be understood that the inventive saw blade design can be used with any known hub for attachment to a handpiece for oscillating the blade.

Although the indicia depicted in FIGS. 5A-5C indicate a cutting depth of 85 millimeters (3.35 inches), other blade sizes may be utilized depending on the intended use. Likewise, the cutting edge width, blade thickness and number of teeth per centimeter can also vary for a given blade. Preferred cutting edge widths range from 19.05 to 29.2 millimeters (0.075 to 1.15 inches). Preferred blade thicknesses range between 0.89 and 1.27 millimeters (0.035 to 0.050 inches). A preferred number of teeth per centimeter for the inventive surgical saw blade is 4.72 (11.99 teeth per inch). The surgical saw blade may be made of any material compatible for surgical use with preferred materials including 420 and 716 series stainless steel grades. A preferred range for the blade hardness is 49 to 54 Rockwell C.

When manufacturing the inventive surgical saw blades, each cutting edge of the tooth is hollow ground by diamond wheels in a bath of refrigerated cutting oil. This technique virtually eliminates heat-induced surface irregularities on the edges and faces of the saw blade. This technique also provides a superior smoothness and shape which reduces abrasion resistance to its lowest level, resulting in a saw blade that stays sharper longer than prior art blades. Other aspects of the manufacturing process can employ conventional processes which are well known in the art and not considered as aspect of the invention.

As such, an invention has been disclosed in terms of preferred embodiments thereof which fulfills each and every one of the objects of the present invention as set forth hereinabove and provides a new and improved surgical saw blade.

Of course, various changes, modifications and alterations from the teachings of the present invention may be contemplated by those skilled in the art without departing from the intended spirit and scope thereof. Accordingly, it is intended that the present invention only be limited by the terms of the appended claims.

We claim:

1. A surgical saw blade comprises
   a) a blade body having opposing side surfaces;
   b) a cutting edge on a distal end of said blade body; and
   c) a means for connecting said blade body to a handpiece adapted to oscillate said blade body;
   d) wherein said cutting edge comprises a plurality of teeth, each tooth comprising:
      i) a generally flat face extending from one of said opposing side surfaces, said generally flat face terminating at a cutting point; and
      ii) a hollow trough having a generally concave surface aligned with the other of said opposing side surfaces and in opposing relationship with said generally flat face;
   e) said plurality of teeth arranged in a pair of rows such that said flat face is adjacent said hollow trough for each side of said blade body.

2. The surgical saw blade of claim 1 wherein said hollow trough has a predetermined radius of curvature.

3. The surgical saw blade of claim 1 wherein said hollow trough is located at a base portion of each tooth.

4. The surgical saw blade of claim 3 wherein a proximal end of said hollow trough joins said side surface of said blade body at a semicircular-shaped edge.

5. The surgical blade of claim 1 wherein said cutting edge has a width approximating a width of said blade body.

6. The surgical blade of claim 1 wherein said cutting edge has a width greater than a width of said blade body.

7. The surgical blade of claim 1 wherein said cutting edge is flared.

8. The surgical saw blade of claim 1 wherein said generally flat face of each said tooth is offset from a plane of a side surface that said tooth extends from such that a thickness of said cutting edge is between about 0.003 and 0.004 inches greater than the thickness of said blade body.

9. The surgical saw blade of claim 8 wherein said thickness of said cutting edge is 0.004 inches greater than the thickness of said blade body.

10. The surgical saw blade of claim 1 wherein said generally flat face terminating at said cutting point forms a 30° angle.

11. The surgical saw blade of claim 1 further comprising a pair of beveled sides, each beveled side disposed between a portion of said hollow trough and a portion of said flat face, said beveled sides joining at a terminating edge at a distal end of each tooth.

12. The surgical saw blade of claim 11 wherein each said beveled side has a 30° bevel.

* * * * *

UNITED STATES PATENT AND TRADEMARK OFFICE
Certificate

Patent No. 5,306,285                                                   Patented: April 26, 1994

On petition requesting issuance of a certificate for correction of inventorship pursuant to 35 U.S.C. 256, it has been found that the above identified patent, through error and without any deceptive intent, improperly sets forth the inventorship. Accordingly, it is hereby certified that the correct inventorship of this patent is:
    Alex M. Miller, Savannah, Ga., Robert L. Stranahan, Ventura, Calif., Brian S. Dense, Lilburn, Ga. and John A. Repar, Ventura, Calif.

Signed and Sealed this Twenty-Eighth Day of July, 1998.

MICHAEL BUIZ, SPE
Art Unit 3731